United States Patent [19]
Putnam

[11] Patent Number: 6,138,079
[45] Date of Patent: Oct. 24, 2000

[54] DEVICE FOR CALCULATING FLUID LOSS FROM A BODY DURING EXERCISE

[76] Inventor: John M. Putnam, 6110 S. 239th St., Kent, Wash. 98032

[21] Appl. No.: 08/912,497

[22] Filed: Aug. 18, 1997

[51] Int. Cl.[7] .................................................. G01C 22/00
[52] U.S. Cl. ........................ 702/50; 364/561; 235/472.01
[58] Field of Search ............................... 702/50; 436/130; 422/59; 482/8; 364/561; 235/472.01

[56] References Cited

U.S. PATENT DOCUMENTS

| | | | |
|---|---|---|---|
| 3,797,010 | 3/1974 | Adlu et al. | 340/323 |
| 4,054,786 | 10/1977 | Vincent | 364/575 |
| 4,220,996 | 9/1980 | Searcy | 364/561 |
| 4,334,190 | 6/1982 | Sochaczevski | 324/171 |
| 4,970,172 | 11/1990 | Kundu | 436/130 |
| 5,174,959 | 12/1992 | Kundu et al. | 422/59 |

OTHER PUBLICATIONS

Kingston, Use of dew–point hygrometry, direct sweat collection, and measurement of body water losses to determine sweating rates in exercising horse, American Journal of Veterinary Research, 175–181, Feb. 1997.

*Primary Examiner*—Patrick Assouad
*Assistant Examiner*—Linh Nguyen
*Attorney, Agent, or Firm*—J. Stewart Brams

[57] ABSTRACT

A device is disclosed in which a housing is adapted for attachment to an athlete's body or clothing during exercise. Physical data about the athlete is entered via a keypad located on the surface of the device. A calculation process then takes the physical data entered by the athlete and calculates the amount of water being lost through dehydration. This information, along with a graphic display of how much water the athlete should drink, is presented on a screen on the surface of the device.

20 Claims, 5 Drawing Sheets

DEVICE FOR CALCULATING FLUID LOSS FROM A BODY DURING EXERCISE

BACKGROUND OF THE INVENTION

1. Field of the Invention

This invention relates to computation devices, more particularly to those devices that provide athletes with information regarding effects of their exercise.

2. Description of the Related Art

There are no devices on the market today that provide feedback to an athlete with respect to his dehydration level. Part of the problem is that dehydration is a gradual process that can occur without the athlete's knowledge.

What is needed is a device that an athlete can use to compute the rate at which he needs to replenish water in his system.

SUMMARY OF THE INVENTION

The device of the present invention includes a housing adapted for attachment to an athlete's body. A few ways in which the device can be attached to the athlete are clipping it to clothing, or possibly attaching it to a wrist band like a watch. Physical data about the athlete is entered via a keypad located on the surface of the device. A calculation process then takes the physical data entered by the athlete and calculates the amount of fluid being lost by sweating and respiration. The calculation process then generates a fluid deficit value, which is the amount of fluid lost minus the amount of fluid replaced, and is the amount of fluid required to re-hydrate the athlete to his or her pre-exercise level. This information, along with a graphic display of the fluid deficit value is presented on a screen on the surface of the device so that the athlete knows how much water to drink.

Because the device is portable and can be worn while the athlete exercises, the athlete can know at any point in time, exactly how much fluid intake is required. Further, because the calculation process can take into account the type of exercise, the athlete's body weight, the temperature, and the relative humidity, the results are individually tailored to that particular athlete for that particular exercise. Still further features and advantages will become apparent from the ensuing description and drawings.

DETAILED DESCRIPTION

General Construction

Figure 1:
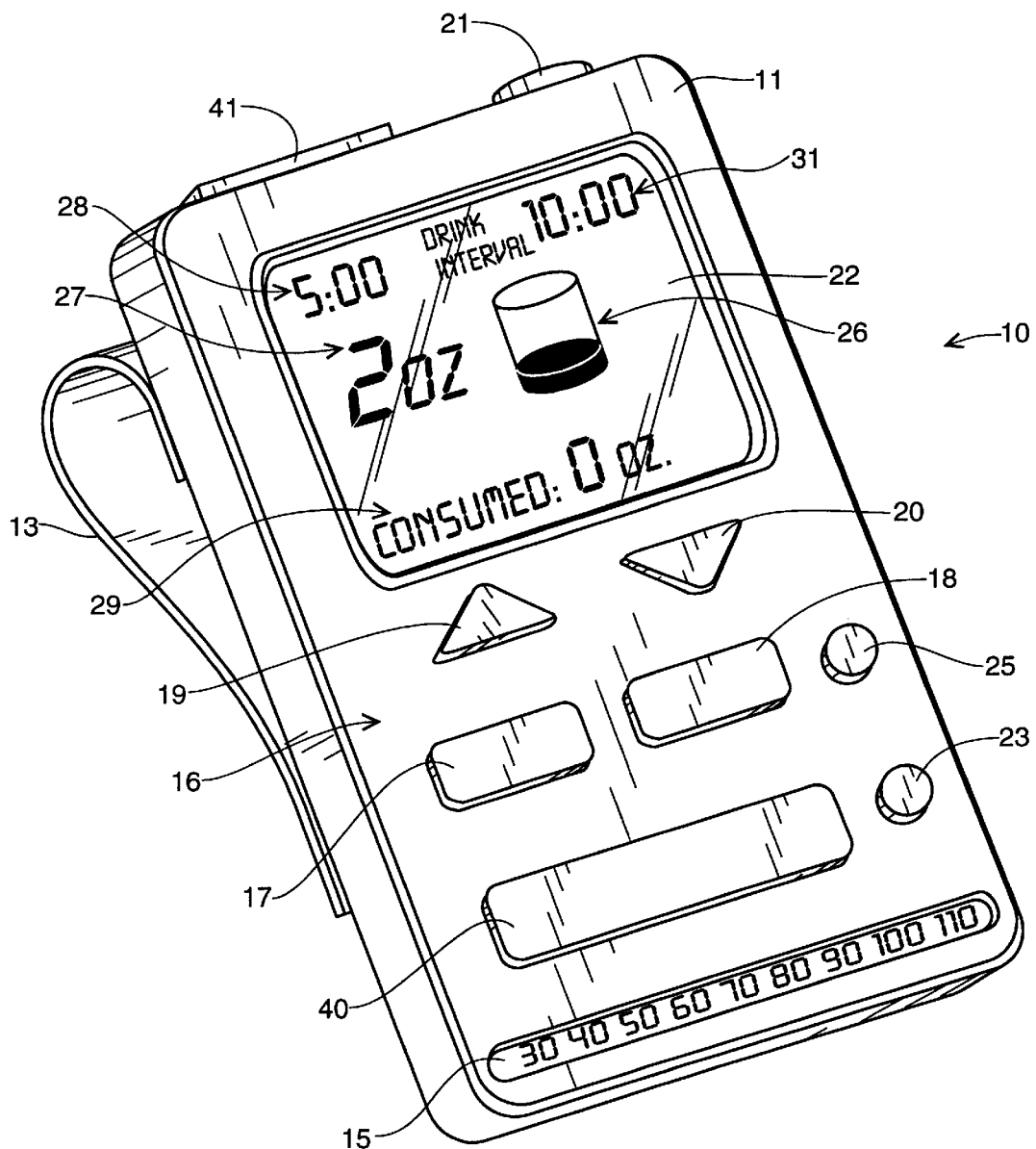
FIG. 1 is a perspective view of the hydration calculation device of the present invention.

FIG. 1 is a perspective view of the hydration calculation device 10 of the present invention. The housing 11 is adapted for attachment to a person's clothing via a clip 13. Further, the housing 11 contains a thermometer 15 for providing an accurate temperature measurement and thus, a more accurate hydration calculation. A keypad 16 is provided on the surface of the device 10 for entering data. The keypad 16 is comprised of a plurality of buttons including a start/stop button 17, a mode button 18, the function of which will be described herein-later, a plus button 19 to increase numerical input values, a minus button 20 to decrease numerical input values, a light button 21 to illuminate a display screen 22, a display button 23 to increase the size of a portion of the display on the display screen 22, a reset button 25, the function of which will be described herein-later, an enter button 40 for finalizing input values, and a hold button 41 for momentarily pausing all functions.

For example, a 150 pound athlete would press the start/stop button 17 to energize the device 10, and would then start inputting data to the device 10. The display screen 22 would flash the input prompt, "WEIGHT: 0," and the athlete would press the plus button 19 to increase the weight input from 0, until it reaches 150. If the athlete passes the intended weight, the minus button will reduce the amount of weight entered. Then, the athlete would hit the enter button 40. This would finalize the weight input value as being equal to 150, and then the next input prompt would flash, for example, "TEMPERATURE: 70 F." When the athlete finishes entering data in this fashion, none of the input prompts will flash. Instead, a message will flash such as "START TIMER." Hitting the enter button 40 at this stage will begin the calculation process as will be described herein-later.

If the athlete wishes to enter data out of sequence, he or she can press the mode button 18 to cycle through the input prompts. For example, when the weight input prompt is flashing, pressing the mode button 18 will cause the temperature input prompt to flash.

The specific buttons and keys described herein, and the method of using them are given to describe one embodiment of the invention, but are not intended to limit the scope of the present invention. Clearly, many combinations of buttons and keys, and methods of using them, could be implemented to provide the results of the present invention, which are to calculate and indicate hydration requirements of an athlete.

Figure 2:
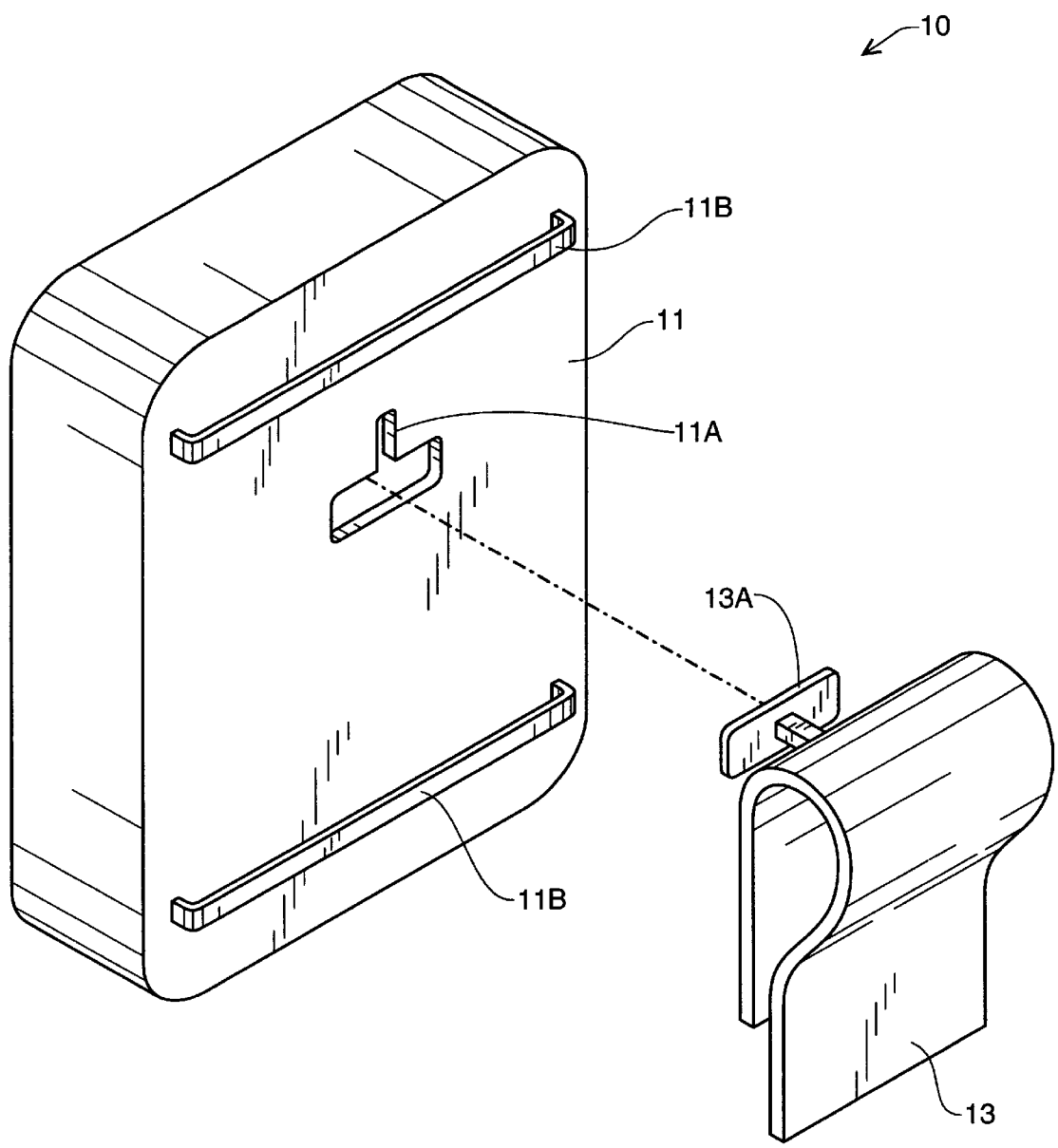
FIG. 2 is a rear perspective view of another embodiment of the device.

FIG. 2 is a rear perspective view of another embodiment of the present invention, in which the clip 13 includes a protruding key 13A which engages within a notch 11A in the housing 11 of the device 10, thus making the clip 13 removable. Two strap receiving loops 11B are formed near opposite ends of the housing 11 for placement of a wrist strap (not shown) therein, so that the device 10 can be worn on a human wrist.

Graphic Display

Referring to FIG. 1, the display screen 22 is configured to display an activity time display 28, which indicates how long the athlete has been exercising, and a drink interval display 31, which indicates the length of time before the athlete will be notified to take another drink. A fluid deficit value numerical display 27 indicates the amount of fluid which has been lost by the athlete, minus the amount that has been replaced by drinking. This value is the amount of fluid which must be consumed by the athlete to completely rehydrate the body to the level it had before the exercise began.

A fluid deficit graphic display 26 indicates a glass which becomes more filled as the drink interval (time until the next drink) decreases to zero. For example, if the desired time between drinks is entered by the athlete as equal to 5 minutes, the glass will be shown empty when the drink interval display 31 shows 5 minutes, which is at the beginning of the drink interval. As the exercise progresses, the drink interval display 31 will continually decrease toward 0, showing the amount of time until the next drink. As this occurs, the graphic display of the glass will show the glass becoming more fill, until it is completely full when the drink interval display 31 indicates zero. This is intended as a graphic reminder that the next drink time is approaching, and that the fluid deficit is continually increasing.

A total ounces consumed display 29 shows the total amount of fluid consumed (replaced) by the athlete during the exercise. This value is calculated from values input by the athlete during the exercise, as will be described herein-later.

As an example of the display, FIG. 1 shows the display for an athlete who has been exercising for 5 minutes, as shown by the activity time display 28. The drink interval is every 15 minutes, and the drink interval display 31 has decreased since the beginning of the exercise, to show that there is now 10 minutes left until the first drink is required. The fluid deficit value is shown by the fluid deficit value numerical display 27, to be equal to 2 ounces. This means that the athlete must replace 2 ounces of fluids to reach his or her pre-exercise hydration level. Because the athlete is still in the first drink interval, he or she hasn't yet consumed any fluids, and the total ounces consumed display 29 shows 0 ounces.

When the drink interval ends, the drink interval display 31 shows zero, and an alarm sounds for a short period of time, and then shuts off. The display will flash, and continue to do so until the condition is acknowledged by the athlete, by pressing the mode button 18 or the reset button 25, as will be described herein-later.

The graphic display described herein is given to describe one embodiment of the invention, but is not intended to limit the scope of the present invention. Clearly, many combinations of display elements could be implemented to provide hydration information to an athlete, and would be within the scope of the present invention.

Block Diagram Description

Figure 3:
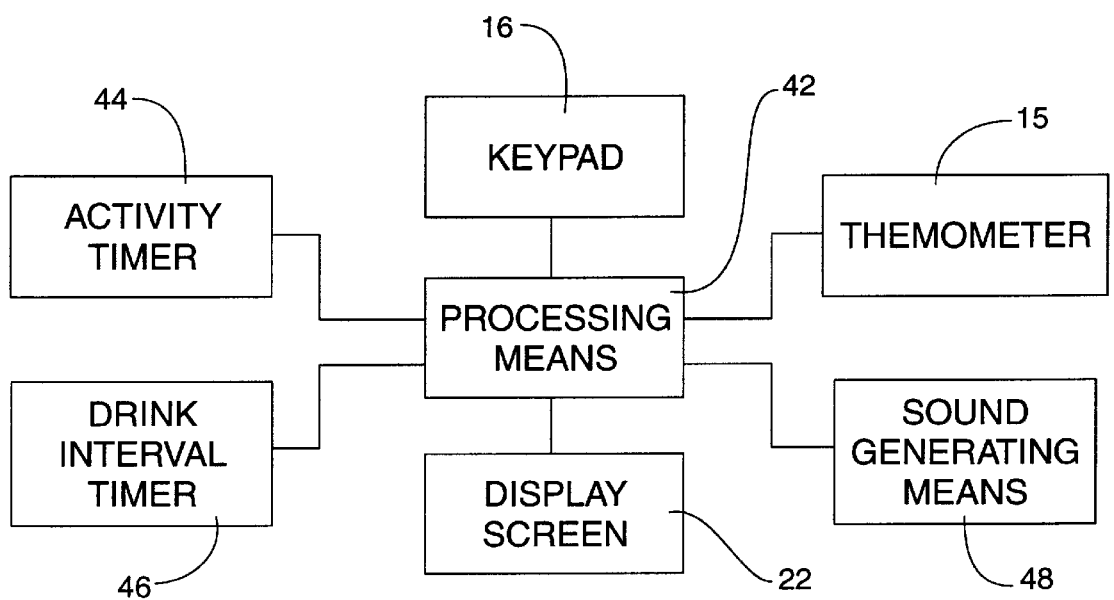
FIG. 3 is a block diagram of the device.

FIG. 3 is a block diagram of the hydration calculation device 10. A processing means 42 which would include electronic circuitry and one or more microchips controls the functions of the device 10 in a known manner. The processing means 42 accepts input from the keypad 16, controls and receives information from the activity timer 44 and the drink interval timer 46, generates a display for the display screen 22, and controls the sound generating means 48 for alarms.

The thermometer 15 may be an electronic type which is tied into the processing means 42, or may be a common self-contained type which is not tied into the processing means 42. In the latter case, the temperature value would have to be input by the athlete for use in the calculation.

Operation Description

Figure 4:
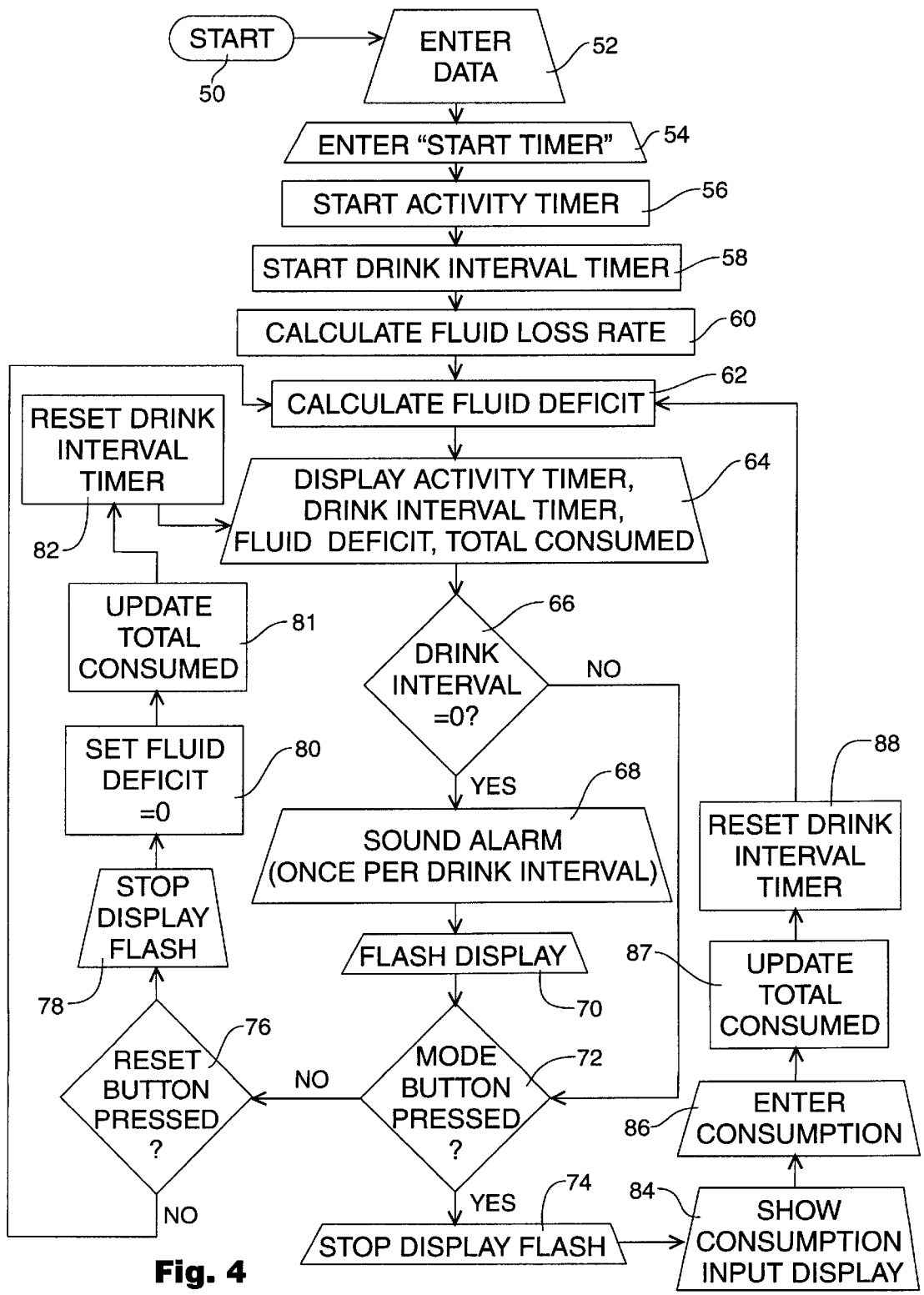
FIG. 4 is a flow chart illustrating the operation of the device.

FIG. 4 is a flow chart illustrating the operation of the device 10. As a convention, this chart uses blocks with curved sides to indicate starting and stopping the process; blocks with straight, parallel sides indicate processing steps; and blocks with straight, non-parallel sides indicate steps involving input or output.

As indicated in block 50, the athlete turns on the device using the start/stop button 17. As shown in block 52, and as described herein-before, the athlete then enters data necessary for fluid deficits to be calculated. Also as described herein-before, a message will flash such as "START TIMER," when the athlete is done inputting data. Hitting the enter button 40 at this stage (block 54), will start the activity timer 44 (block 56) and the drink interval timer 46 (block 58), and will cause the processing means 42 to begin the calculations.

In block 60, the processing means 42 calculates a fluid loss rate. This is the rate at which fluid will be lost by the athlete. This value is in units of quantity of fluid per unit time, such as ounces per hour. In block 62, the fluid deficit is calculated, which is the total amount of fluid lost, minus the total amount of fluid consumed.

In block 64, the activity time display 28, the drink interval display 31, the fluid deficit value numerical display 27, the fluid deficit graphic display 26, and the total ounces consumed display 29 are all shown on the display screen 22.

In block 66, if the drink interval timer 46 has reached zero, an alarm will sound in block 68, and the display will begin to flash in block 70. As indicated in blocks 72, 74, 76 and 78, the display will continue to flash until the condition is acknowledged by pressing either the mode button 18, or the reset button 25. If neither the mode button 18 or the reset button 25 are pressed, the display continues to flash, and the process returns to block 62 to update the calculation and the display of the fluid deficit.

If the reset button 25 is pressed, the display stops flashing in block 78 as described above, the fluid deficit is reset to 0 (block 80), the total consumed value is updated (block 81), and the drink interval timer 46 is reset (block 82) to the value selected by the athlete during the input stage (block 52) of the process. Then the process continues with block 64 to update the display. The reset button 25 is pressed by the athlete to indicate that he or she has replaced the total amount of the fluid deficit.

If the athlete drinks less or more than the total amount of the fluid deficit, then he or she presses the mode button 18 instead of the reset button 25. The display stops flashing in block 74 as described above, and the consumption display 33 (see FIG. 4) is shown on the display screen 22 (block 84).

Figure 5:
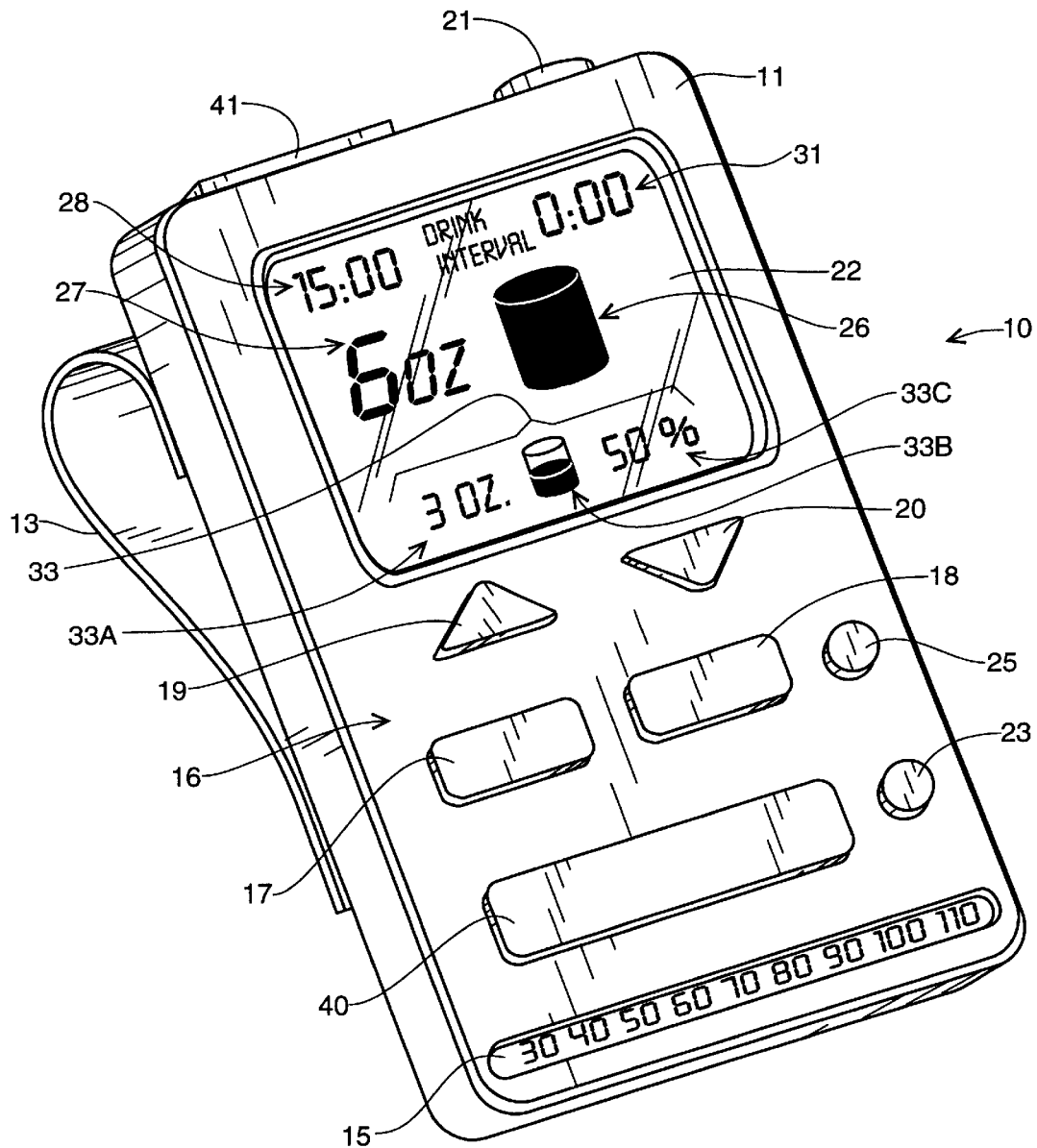
FIG. 5 is a perspective view of the device, shown when the consumption input display is on the display screen.

FIG. 5 is a perspective view of the device 10, shown when the consumption input display 33 is on the display screen 22. This display facilitates entry of the amount of fluid consumed by the athlete (block 86). The athlete presses the plus button 19 or the minus button 20 until the actual amount of fluid consumed appears on the consumption numerical display 33A. Pressing the enter button 40 finalizes this input value. A consumption graphical display 33B indicates the percentage of the fluid deficit value which appears on the consumption numerical display 33A. For example, if the fluid deficit value is 6 ounces and 3 ounces are shown, the graphic image of the glass will be half full. The consumption percentage display 33C numerically indicates this percentage. In this example, wherein in 3 ounces are shown and the fluid deficit value is 6 ounces, the percentage indicated would be 50.

The process continues with block 87, wherein the total consumed value is updated. In block 88, the drink interval timer 46 is reset. The process then continues with block 62, wherein the fluid deficit is re-calculated and the display is updated.

As can be seen by following the "NO" flow arrow out of the drink interval decision box 66, the athlete can indicate that he or she has replaced fluids at any time by pressing the mode button 18 or the reset button 25. He or she does not have to wait for the drink interval timer 46 to reach zero.

The flow chart just described illustrates one embodiment of the invention, but is not intended to limit the scope of the present invention. Clearly, other processes could be implemented to provide the results of the present invention, which are to calculate and indicate hydration requirements of an athlete.

Methods of Calculating the Fluid Loss Rate

A well known scale for use in determining energy expended during physical activity is the MET scale. One MET is equal to one kilocalorie per hour per kilogram of body weight. Some examples from the MET scale are:

| Physical Activity | MET Range |
|---|---|
| Backpacking | 5–11 |
| Bicycling (10 mph) | 7 |
| Downhill Skiing | 5–8 |
| Running (10 km per hour) | 10 |
| Running (16 km per hour) | 16 |

The source of the above information is the American College of Sports Medicine, Guidelines for Graded Exercise Testing and Exercise Prescription, Philadelphia: Lea & Febiger, 1986. Some of the numbers from the published scale are rounded herein to whole numbers for simplicity. As an example of how METS are applied, assume that a person weighing 70 kg is running at 10 kilometers per hour. The kilocalories expended per hour will be 10 kcal per hour per kg * 70 kg =700 kcal per hour. This energy will be lost by the body as heat to the environment, to avoid overheating of the body. This is accomplished by the body's own internal temperature regulation system, through sweat loss, as well as through radiation, convection, and respiration. Radiation and convection represent dry, or sensible heat loss. Sweat loss represents latent heat loss, and respiration represents a combination of both sensible and latent heat loss.

Thus, $THL_R$=METS * W, wherein $THL_R$ is the rate of total heat lost by the body in kilocalories per hour, METS is $THL_R$ per kilogram of body weight, and W is body weight in kilograms.

An approximation of the rate of fluid lost by the body, $FL_R$, via sweat and respiration in ounces per hour, can be made by dividing the latent heat of vaporization of water, L, in kilocalories per ounce into the rate of total heat loss, $THL_R$, in kilocalories per hour. L is equal to 17.27 kilocalories per ounce, based on a skin temperature of 96.8 F.

Using the above example of a 70 kg man running at 10 km per hour, with a MET rating of 10, $THL_R$ thus being equal to 700, $FL_R$ is equal to $THL_R$/ L=700/17.27=40.5 ounces per hour.

This equation, $FL_R$=$THL_R$/L, is an approximation. It does not account for the fact that not all of the sweat produced by the human body will have a cooling effect. Some sweat will roll off of the body without being evaporated, and some sweat will be absorbed by clothing. If factors accounting for this were applied to the equation, they would have the effect of increasing the calculated $FL_R$.

Furthermore, as stated above, not all of the heat lost to the environment is latent. In other words, the heat lost by sweating and the latent portion of respiration is less than the total heat lost to the environment by all avenues, which include sweating, respiration, convection, and radiation. If factors accounting for this were applied to the equation, they would have the effect of decreasing the calculated $FL_R$.

It has been found that the equation, $FL_R$=$THL_R$/L provides fairly reliable results when compared to real world examples of fluid loss by athletes, even though it does not include the above described factors; thus, it is a useful approximation of fluid loss rate.

Because some of the unapplied factors discussed above would have the effect of increasing $FL_R$, while others would have the effect of decreasing $FL_R$, they may indeed have an overall negligible effect on fluid loss rate, considering the fairly reliable results found when the equation is applied to real world examples.

This equation, $FL_R$=$THL_R$/L gives fluid loss rate in ounces per hour. This is the fluid loss rate calculated in block 60 of FIG. 4. Total fluid lost is found by multiplying the fluid loss rate by the time spent in the activity (block 56), and fluid deficit (block 62) is found by subtracting the total amount consumed (blocks 81 and 87) from the total fluid lost.

Although the equation, $FL_R$=$THL_R$/L is useful, it would be desirable to account for additional factors such as temperature and humidity, when calculating fluid loss rate. A new, empirically derived equation calculates a fluid loss rate $FL_R$ using the MET scale, body weight W in kg, temperature T in degrees Fahrenheit, and humidity H. The new calculation is as follows:

$FL_R$=(METS *W * T+$H^2$)/ 1450, or $FL_R$=($THL_R$ * T+$H^2$) / 1450.

Using the example already given, of a person weighing 70 kg and running at 10 kilometers per hour, and further assuming a temperature of 80 F. and a relative humidity of 50%, the calculation would be as follows: $FL_R$=(10 METS * 70 kg * 80 +502) / 1450 =40.3 ounces per hour. Recall that the equation, $FL_R$=$THL_R$/L yielded 40.5 ounces per hour for the same example.

One study by the American College of Sports Medicine reports that fluid losses of 51 ounces per hour are common in endurance sports, and 85 ounces per hour have been measured in extremely hot and humid conditions. Assuming a 150 lb. (68 kg) body weight, 7 minutes per mile pace (13.7 km per hour =13.7 METS), 80 degree F. air temperature and 50% relative humidity, the calculated fluid loss rate using the first equation would be $FL_R$=$THL_R$/L =METS * W / L=13.7 * 68 / 17.27 =54 ounces per hour. Using the second equation, the fluid loss rate would be $FL_R$=(13.7 METS * 68 kg * 80+502) / 1450=53 ounces per hour.

Assuming extremely hot weather of 90 degrees F. and 70% relative humidity, a pace of 5 minutes per mile (19.2 km per hour =19.2 METS), and the same body weight of 68 kg, the calculated fluid loss rate using the second equation would be $FL_R$=(19.2 METS * 68 kg * 90 +$70^2$) / 1450 =84 ounces per hour.

The above calculations provide reasonable results which fall into the ranges of fluid losses reported by the American College of Sports Medicine.

Either of the calculations presented herein for calculating $FL_R$ may be used in the present invention, or any other formula which provides adequate results. It is also possible to estimate energy expenditure, and thus rate of heat loss, using heart rate, which can be either input into the device 10, or read by the device 10. Acumen, Inc., based in Hong Kong and Virginia, manufactures a heart rate monitor which converts the heart rate to an estimate of energy expenditure. The present invention could be made to monitor heart rate directly using this technology, convert the heart rate to an estimate of energy expenditure, and use this information to calculate the rate of fluid loss in the manner already described herein.

Other embodiments are possible. For example, the device could be configured to ignore replaced fluids, and calculate and display fluid lost only, without a calculation of fluid deficit. Such a device would not require any inputs by the user during exercise. In such a case, the athlete should have a drinking container with measurements marked thereon, so that the athlete can keep track of how much fluid has been replaced.

In another embodiment, the athlete would not be permitted to enter a value of consumed fluids which is different from the fluid deficit. The reset button 25, which is used when the entire deficit has been replaced, would still be provided.

With any of the embodiments described herein, the activity timer 44 or the drink interval timer 46 can be deleted, of course with associated losses in benefits.

The foregoing description is included to describe embodiments of the present invention which include the preferred embodiment, and is not meant to limit the scope of the invention. From the foregoing description, many variations will be apparent to those skilled in the art that would be encompassed by the spirit and scope of the invention. Accordingly, the scope of the invention is to be limited only by the following claims and their legal equivalents.

What is claimed is:

1. A device for computing a person's fluid loss during physical exercise, comprising:
   a. a housing;
   b. an input means accessible from the exterior of said housing and selectively operable to enter data for calculating a person's fluid loss;
   c. a calculation means disposed within said housing and configured to calculate a person's fluid loss based on data entered by selective operation of said input means; and
   d. a display means for displaying the fluid loss calculated by said calculation means.

2. The device of claim 1, wherein said input means comprises a mode control to switch between input prompts shown on said display means, a plus control to increase numerical input values, a minus control to decrease numerical input values, and an enter control to finalize input values.

3. The device of claim 1, wherein the calculation means determines the fluid loss by performing the steps of:
   a. establishing a rate of heat loss;
   b. multiplying the rate of heat loss by a time of exercise to establish a total heat loss; and
   c. dividing the total heat loss by a value to establish the fluid loss.

4. The device of claim 3, wherein the rate of heat loss is established by establishing a rate of heat loss per unit of body weight, based on an input activity level, and multiplying the rate of heat loss per unit of body weight by an input body weight.

5. The device of claim 3, wherein the device is configured to monitor a heart rate of the person, and wherein the rate of heat loss is based on the heart rate.

6. The device of claim 3, wherein the value is substantially equal to a latent heat of vaporization of water at a skin temperature of substantially 96.8 degrees Fahrenheit.

7. The device of claim 1, wherein the calculation means determines the fluid loss by performing the steps of:
   a. establishing a rate of heat loss;
   b. multiplying the rate of heat loss by an air temperature to establish a product;
   c. adding the product to a square of a humidity level to establish a sum;
   d. dividing the sum by a factor to establish a fluid loss rate; and
   e. multiplying the fluid loss rate by a time of exercise to establish the fluid loss.

8. The device of claim 7, wherein the rate of heat loss is established by establishing a rate of heat loss per unit of body weight, based on an input activity level, and multiplying the rate of heat loss per unit of body weight by an input body weight.

9. The device of claim 7, wherein the device is configured to monitor a heart rate of the person, and wherein the rate of heat loss is based on the heart rate.

10. The device of claim 7, wherein the factor is substantially equal to 1450.

11. A device for computing a person's fluid deficit during physical exercise, comprising:
    a. a housing;
    b. an input means accessible from the exterior of said housing and selectively operable to enter data for calculating a person's fluid loss;
    c. a calculation means disposed within said housing and configured to calculate a person's fluid loss based on data entered by selective operation of said input means;
    d. said calculation means being further configured to subtract an input amount of fluid consumed by a person from the person's fluid loss to establish a fluid deficit value; and
    e. a display means for displaying said fluid deficit value.

12. The device of claim 11, wherein said input means comprises a mode control to switch between input prompts shown on said display means, a plus control to increase numerical input values, a minus control to decrease numerical input values, and an enter control to finalize input values.

13. The device of claim 11, wherein the calculation means determines the fluid loss by performing the steps of:
    a. establishing a rate of heat loss;
    b. multiplying the rate of heat loss by a time of exercise to establish a total heat loss; and
    c. dividing the total heat loss by a value to establish the fluid loss.

14. The device of claim 13, wherein the rate of heat loss is established by establishing a rate of heat loss per unit of body weight, based on an input activity level, and multiplying the rate of heat loss per unit of body weight by an input body weight.

15. The device of claim 13, wherein the device is configured to monitor a heart rate of the person, and wherein the rate of heat loss is based on the heart rate.

16. The device of claim 13, wherein the value is substantially equal to a latent heat of vaporization of water at a skin temperature of substantially 96.8 degrees Fahrenheit.

17. The device of claim 11, wherein the calculation means determines the fluid loss by performing the steps of:
    a. establishing a rate of heat loss;
    b. multiplying the rate of heat loss by an air temperature to establish a product;
    c. adding the product to a square of a humidity level to establish a sum;
    d. dividing the sum by a factor to establish a fluid loss rate; and
    e. multiplying the fluid loss rate by a time of exercise to establish the fluid loss.

18. The device of claim 17, wherein the rate of heat loss is established by establishing a rate of heat loss per unit of body weight, based on an input activity level, and multiplying the rate of heat loss per unit of body weight by an input body weight.

19. The device of claim 17, wherein the device is configured to monitor a heart rate of the person, and wherein the rate of heat loss is based on the heart rate.

20. The device of claim 17, wherein the factor is substantially equal to 1450.

* * * * *